United States Patent [19]

Leininger et al.

[11] Patent Number: 4,907,308
[45] Date of Patent: Mar. 13, 1990

[54] HEAT EXCHANGE SYSTEM FOR INFLATABLE PATIENT SUPPORT APPLIANCES

[75] Inventors: Peter A. Leininger, San Antonio, Tex.; Mohamad A. Hajianpour, Miami, Fla.

[73] Assignee: Kinetic Concepts, Inc., San Antonio, Tex.

[21] Appl. No.: 274,273

[22] Filed: Nov. 21, 1988

[51] Int. Cl.⁴ .................. A47C 27/10; A47G 7/04
[52] U.S. Cl. .................................... 5/455; 5/453; 5/421; 5/462; 62/261; 165/46
[58] Field of Search ............... 5/453, 455, 469, 441, 5/449, 421, 422, 462; 62/261; 165/46

[56] References Cited
U.S. PATENT DOCUMENTS

| | | |
|---|---|---|
| 800,967 | 10/1905 | Young et al. ........................ 5/422 |
| 1,121,277 | 12/1914 | Mitchell . | |
| 2,998,817 | 9/1961 | Armstrong . | |
| 3,266,064 | 8/1966 | Figman ........................ 5/469 |
| 4,114,620 | 9/1978 | Moore et al. . | |
| 4,631,767 | 12/1986 | Carr et al. ........................ 5/453 |
| 4,638,519 | 1/1987 | Hess ........................ 5/453 |
| 4,768,249 | 9/1988 | Goodwin ........................ 5/455 |

*Primary Examiner*—Alexander Grosz
*Attorney, Agent, or Firm*—Cox & Smith Inc.

[57] ABSTRACT

A heat exchange system for cooling and/or heating the patient support surface of an inflatable support appliance such as a low air loss bed is disclosed. Tubing and bladders carrying a circulating heat exchange medium is used to locally heat or cool the air within the inflatable cushion, transferring heat to or away from the patient supporting surface. Specially designed cushions with pouches for hold the bladders in close proximity to the supporting surface without compromising the uniform support characteristics of the low air loss bed.

7 Claims, 3 Drawing Sheets

HEAT EXCHANGE SYSTEM FOR INFLATABLE PATIENT SUPPORT APPLIANCES

FIELD OF THE INVENTION

The present invention relates to a system for cooling and/ or heating the patient supporting surface of an inflatable support appliance. The advantages of the system as well as the particular problems solved by this invention are discussed below.

BACKGROUND OF THE INVENTION

Inflatable support appliances use inflatable cushions or air bags as the supporting surface for a patient. By using a fluid support medium such as air within the bags, an irregularly shaped body placed on top of the air bags will deform the supporting surface in such a manner so as to provide a more uniform distribution of load bearing pressure points than can be attained with a conventional mattress. When a patient lies supinely on a flat surface, or even on a conventional mattress, most of the load is born by protuberances of the posterior surface of the body such as the heels, the buttocks, the scapulae, and the occipital region of the head. The relatively small areas of soft tissue at these points are then subjected to high pressures by being compressed between the skeleton and the supporting surface. When this pressure becomes great enough to cause collapse of small capillaries and veins, pressure sores may result. Inflatable support appliances, by uniformly distributing the supporting pressure points along the body surface, reduce the pressure at these critical areas.

One species of inflatable support appliances, called low air loss beds, utilizes a continuous flow of air through the bags from a source of pressurized air (or other gas) such as a blower, the air being exhausted through separate outlets or pores in the fabric of the bags. One of the first such beds is described in U.S. Pat. No. 3,822,425 issued to Scales, the disclosure of which is hereby incorporatd by reference. Low air loss beds are particularly advantageous when the patient support surface of the bags is made from a fabric permeable to water vapor such as GORE-TEX fabric. Patients are predisposed to pressure sores by the accumulation of moisture at the skin surface. By maintaining a low water vapor concentration within the bags with a continuous flow of air, accumulated moisture can diffuse from the patient's skin across the fabric of the patient support surface.

One problem associated with inflatable support appliances, however, comes about when it is desired to cool the patient support surface. These occasions may arise in treating burn patients as well as other types of febrile patients. It may also be desired to heat the patient support surface. In either case, the usual method is to interpose a cooling (or heating) pad between the patient and the support surface. The obvious disadvantage with this practice, however, is that it compromises the uniform supporting characteristics of the inflatable cushions. Furthermore, in the case of low air loss beds, the moisture removing function is also compromised.

With low air loss beds, which use a continuous flow of air, an alternative solution would seem to be to cool the air as it exits from the blower. Due to the large volume of air circulated over a period of time, however, this method is prohibitively expensive. Furthermore, any cooling unit which cooled that large a volume of air would necessarily raise the ambient temperature of the room to uncomfortable levels.

There have been attempts in the past to provide inflatable cushions or mattresses containing tubing through which a heating or cooling medium is circulated. U.S. Pat. No. 800,967 discloses one such device. In this device, however, the tubing carrying the cooling or heating medium is mounted near the bottom of the mattress so that the tubing does not touch the supporting surface of the mattress. Therefore, heat transfer between the supporting surface and the cooling or heating medium must occur through the interposed air within the mattress. This necessarily limits the efficiency of the heat transfer process since air is a very poor heat conductor. Another disadvantage with arrangements of this type is that it is difficult to remove the tubing, if it can be removed at all, in order to wash the mattress or cushions in conventional washing machines.

SUMMARY OF THE INVENTION

The present invention is directed toward providing a solution to the problem described above regarding cooling (or heating) the patient support surface of inflatable support appliances, particularly low air loss beds. In accordance with the present invention, a bladder carrying a circulating heat exchange medium is supported within the inflatable cushion to either provide localized cooling of the air near the patient support surface or physically contact the patient support surface from within the cushion in order to effect more efficient heat transfer and at the same not interfere with the uniform supporting characteristics. By supporting the heat exchange bladder just underneath the patient support surface within the cushion, heat transfer between the patient and the circulating heat exchange medium is facilitated without compromising the uniform supporting characteristics of the cushion and, in the case of a low air loss bed, without interfering with the moisture removal function since a layer of air continues to circulate between the bladder and the patient support surface. Each bladder is supported within the cushion by means of a pouch affixed to the walls of the cushion. An air passageway allows air within the cushion to continue to circulate between the bladder and the inner surface of the patient support surface when the pressure within the cushion is sufficiently high. The location of the bladders just beneath the patient support surface still allows heat transfer to occur in this situation through the relatively thin layer of interposed air.

At areas of localized high pressure, however, the inner surface of the patient support surface physically contacts the bladder. It may even be desirable to lower the air pressure within the cushions in order to provide more extensive areas of such contact since the heat transfer is facilitated when there is no interposing layer of air. The uniform supporting characteristics of the bed are maintained even at those areas of physical contact, however, by circulating the heat exchange medium through the bladders at relatively low pressure. When multiple bladders are used in multiple cushions in accordance with the present invention, groups of bladders are fed with the heat exchange medium from a common manifold so as not to necessitate the use of high flow pressures in order to circulate the medium through the multiple bladders. The uniform supporting characteristics are then maintained by both the low pressure of the circulating heat exchange fluid within the bladder and the fact that the bladder is partially supported by air pressure within the cushion.

The bladder may be easily removed when it is necessary to wash the cushions and reinserted into the pouch afterwards. The pouch also serves to connect the side walls of the cushion in a manner which maintains the shape of the cushion as it is inflated.

DETAILED DESCRIPTION OF THE PREFERRED EMBODIMENT

Figure 1:
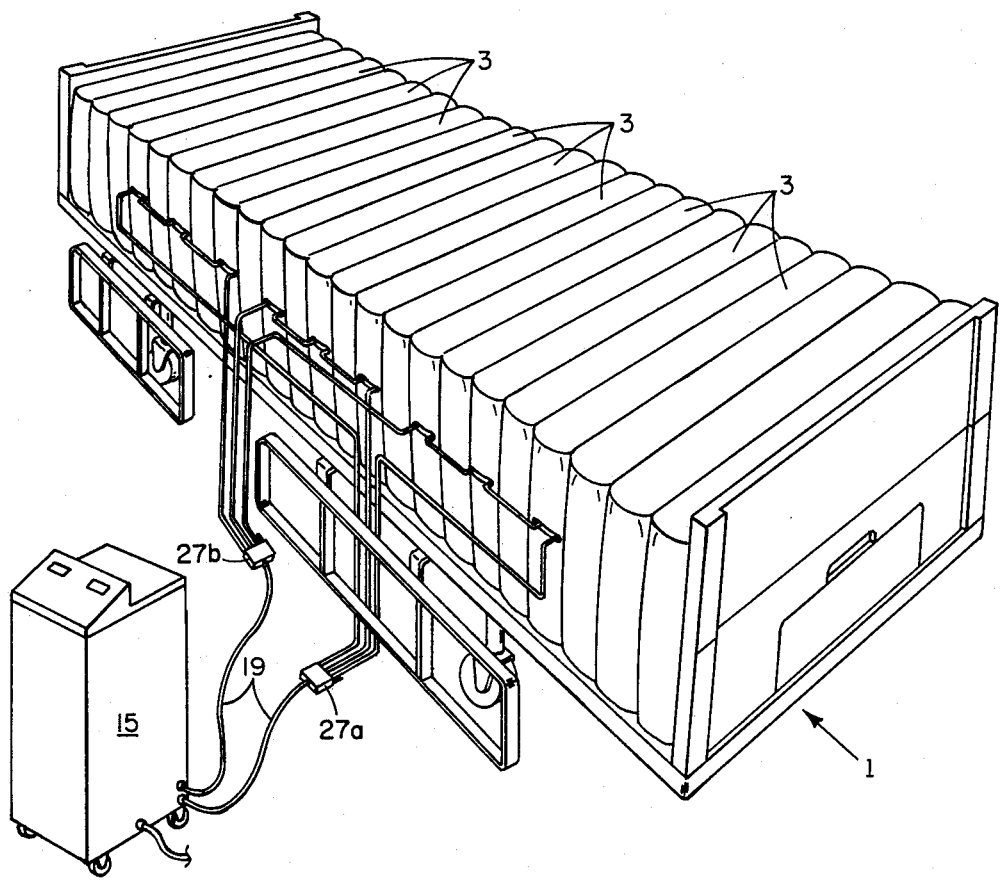
FIG. 1 is a view of a low air loss bed with a cooling system in accordance with the present invention.
Figure 3:
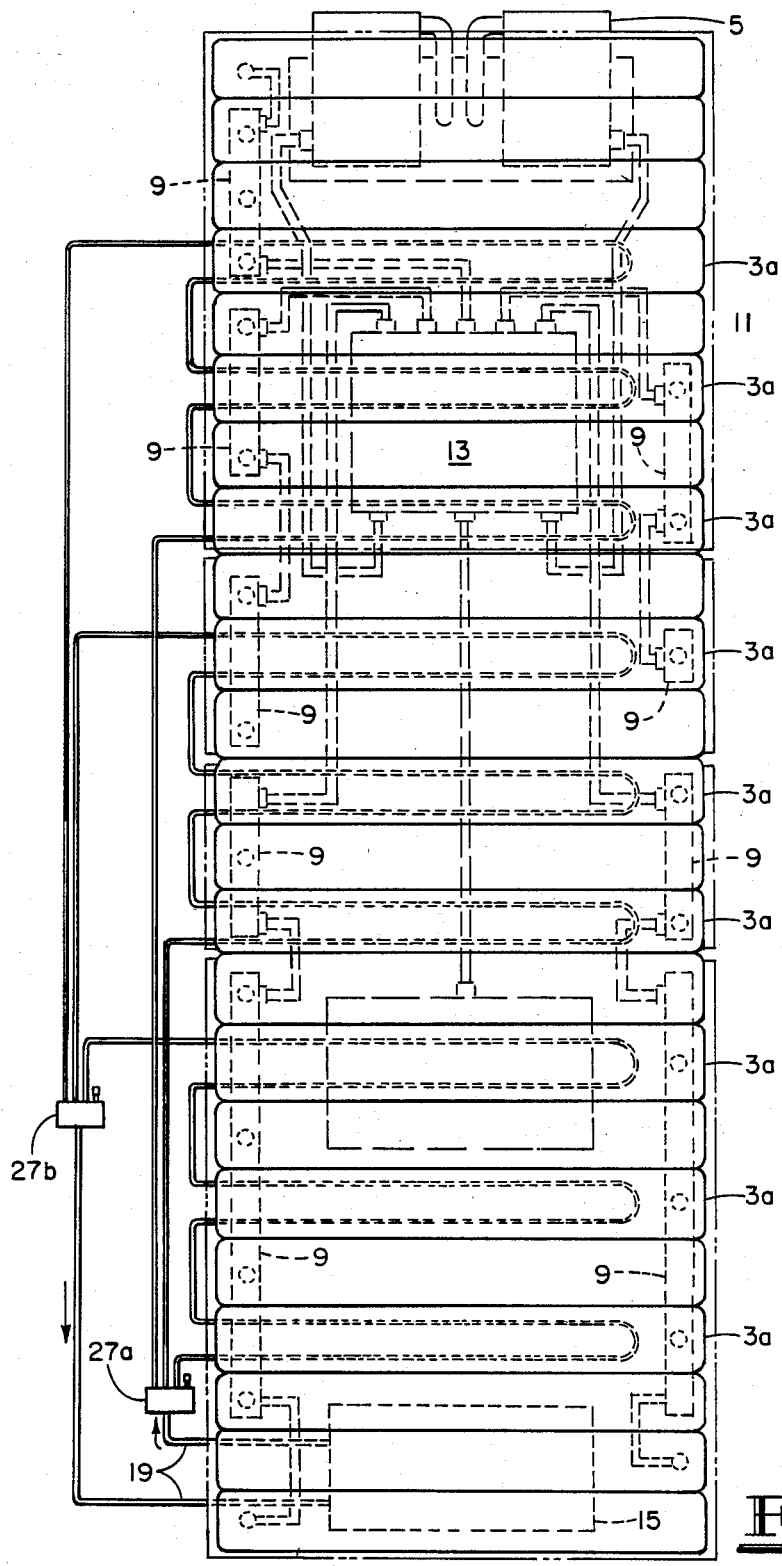
FIG. 3 is a schematic of the low air loss bed in FIG. 1 showing the air supply system.

Referring to FIGS. 1 and 3, there is shown a drawing of a low air loss bed with a cooling system in accordance with the present invention. Inflatable cushions 3 are mounted transversely on a bed frame 1. A blower 5, either mounted on the frame 1 or free-standing, forces air (or other gas) into an air box 13 which then exits under pressure through air hoses 11 feeding a plurality of air manifolds 9. Each air manifold 9 feeds air to a group of the cushions 3 through air inlet nipples 4 located on the bottom of each cushion. A valving arrangement (not shown) allows an operator to control the flow of air to each manifold via a control panel (also not shown). The pressurized air maintains the cushions in an inflated state when a patient lies on the patient supporting surface 3a of each cushion 3. When the top surface 3a is made of water vapor permeable material, a continuous flow of air to remove accumulated water vapor is achieved by the slow escape of air through pores in the fabric forming the other surfaces of the cushions. Other equivalent means, of course, may also be used to allow the escape of air such as separate exhaust ports.

Figure 2:
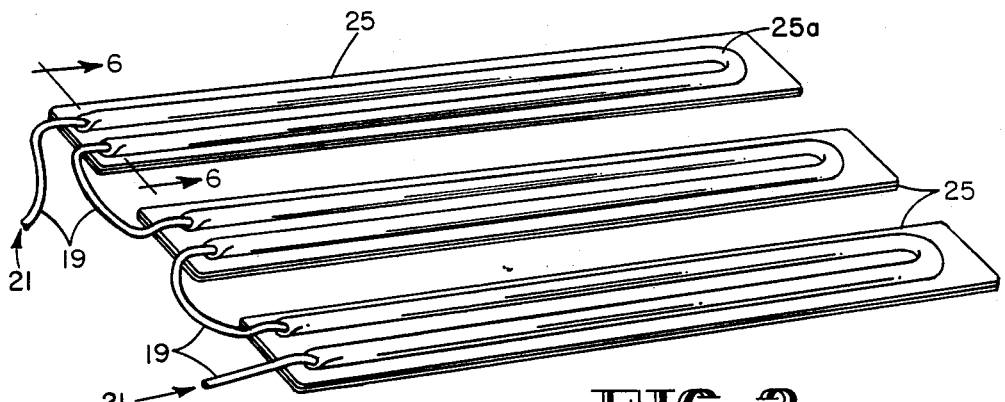
FIG. 2 shows a set of three heat exchange bladders which insert into pouches of the inflatable cushions.
Figure 6:
FIG. 6 is a cross-section of a heat exchange bladder.

In order to cool (or heat) the patient supporting surface 3a of selected cushions 3, heat exchange tubing 19 carrying circulating heat exchange fluid 21 is supported within the selected cushions. In accordance with the present invention, loops of the tubing 19 connect to heat exchange bladders 25 which are inserted into a pouch 23 of each selected cushion. Each of the bladders 25 is made of flexible material and contains a conduit loop 25a through which the heat exchange fluid circulates. A bladder in accordance with the present invention may be made by heat bonding two strips of materials together in a manner leaving the aforementioned conduit loop and inlet and outlet ports for the tubing connections. FIG. 6 is a cross-section of a representative bladder showing the conduit loop, and FIG. 2 shows a set of bladders 25 serially connected by tubing segments. The pouches 23 are located near the superior part of the patient support surface 3a from within the cushion so heat transfer may occur locally between the air contacting the surface 3a and the heat exchange fluid circulating within the bladder. A patient lying on the top surface 3a can either lie above the bladders 25 or can make physical contact with the bladders 25. It may even be desireable to lower the air pressure within the cushions in order to increase the areas of direct contact between the bladders and the patient via the top supporting surface 3a. Pouches 23 are connected to the side walls 3c of the cushions 3 allowing the bladders to be partially supported by the air pressure within the cushion. Since the fluid pressure within the bladders is also kept relatively low, the uniform supporting characteristics of the cushions are maintained even when the patient contacts the bladders.

Heat exchange fluid 21 is made to circulate through the tubing 19 by means of a pump, which may be of any conventional design. In order to dissipate the heat transferred from the patient support surfaces 3a, the fluid is pumped through a refrigeration unit, which is also of conventional design. In a presently preferred embodiment, both the refrigerator and pumping functions are accomplished by a single unit 15, which contains both a fluid pump and a refrigerator. In alternative embodiments, the refrigeration unit may be replaced by an ice bath, or if it is desired to heat the patient support surface, by any appropriate heating means.

As illustrated in FIG. 1, tubing 19 is connected to the outlet of refrigeration and pumping unit 15. A heat exchange fluid, such as water, is pumped through tubing 19 to outlet fluid manifold 27a which feeds in a parrallel fashion a plurality of heat exchange bladders 25 inserted into selected pouches 23 of air cushions 3. FIG. 1 shows the manifold 27a feeding three sets of bladders with each set consisting of three bladders. Segments of tubing 19 are connected to the inlets and outlets of the sets of bladders 25 in a series fashion to enable all the bladders of the set to be fed from the single manifold 27a. In a presently preferred embodiment, only three separate bladders are series connected since chaining more of the bladders together in this fashion would lessen the efficiency of the heat transfer and increase flow resistance. An increase in flow resistance would necessitate an increased flow pressure in order to circulate the heat exchange fluid through the bladders. This in turn would interfere with the uniform supporting characteristics of the bed when the patient makes physical contact with the bladders. According to the present invention, therefore, a common outlet manifold is used to feed a plurality of bladders in order to maintain a low flow resistance. After circulating through the conduit loops 25a of each bladder, the heat exchange fluid is returned to the refrigeration and pumping unit 15 via inlet fluid manifold 27b where it is circulated through the unit and cooled before being returned to the bladders.

Figure 4:
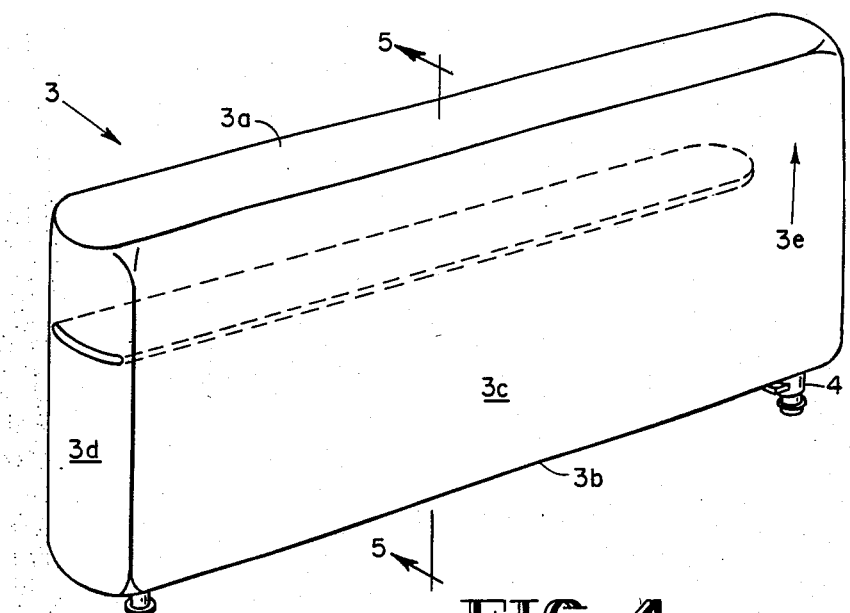
FIG. 4 is a perspective view of an inflatable cushion in accordance with the present invention.
Figure 5:
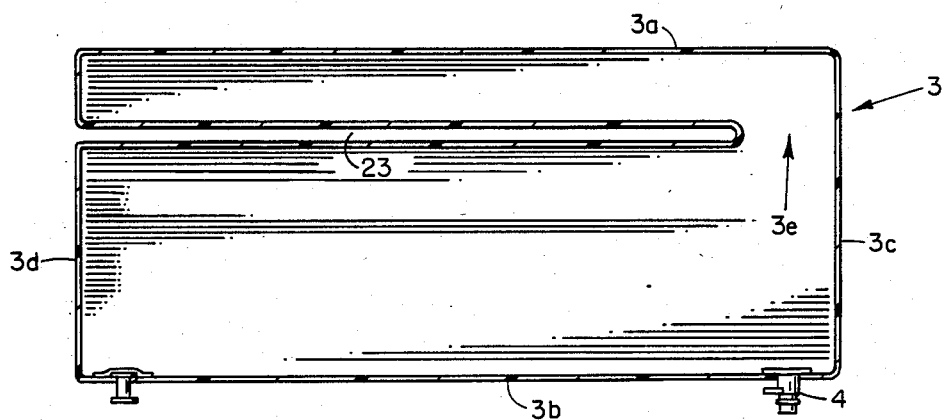
FIG. 5 is a cross-section of the cushion in FIG. 4.

In FIGS. 4 and 5, there is shown a representative cushion 3 in accordance with the present invention. A pouch 23, as described above, is continuous with end wall 3d and extends longitudinally within the cushion. The pouch is connected to each adjacent side wall 3c all along its length, thereby fixing the position of the pouch with respect to the side walls. In order that the flow of air toward the top surface 3a is left unimpeded, the pouch 23 does not extend all the way to the opposite end wall 3d thus forming an air passageway 3e through which air can flow. Even when the pressure within a cushion is low enough so that the patient support surface 3a directly contacts the bladder, the normal periodic movement of the patient is usually enough to cause temporary separation of the bladder from the underside of the patient support surface 3a which allows air to flow through passageway 3e and remove accumulated moisture. Alternatively, the operator may periodically increase the pressure within the cushion to produce a layer of air between the patient and the bladder.

The pouch 23 may be stitched or otherwise connected to each of the two side walls 3c all along the length of the pouch. Thus, the pouch also serves to prevent the cushion from flattening out due to separation of the side walls caused by air pressure within the cushion.

Although the invention has been described in conjunction with the foregoing specific embodiment, many alternatives, variations and modifications are apparent to those of ordinary skill in the art. Those alternatives, variations and modifications are intended to fall within the spirit and scope of the appended claims.

What is claimed is:

1. A generally elongate inflatable cushion for use with a plurality of similar cushions in inflatable patient support appliances in conjunction with heat exchange tubing, comprising:
    a top patient support surface, two side walls, two end walls, a bottom, and an air inlet nipple; and
    a pouch formed in one of the end walls and connected to each of the opposite side walls within the cushion but not extending to the opposite end wall, said pouch being located between the top patient support surface and the bottom of the cushion and being adapted to removably retain heat exchange tubing.

2. The cushion as set forth in claim 1 wherein the pouch is stitched all along the length of the pouch to each of the opposite side walls.

3. An inflatable patient support appliance, comprising:
    a plurality of inflatable cushions, each having a top surface, a bottom, two end walls, two side walls, and an air inlet port;
    a bed frame for transversely mounting the inflatable cushions thereon such that the top surfaces of the cushions collectively form a patient support surface;
    means for connecting a source of pressurized air to the air inlet ports of the inflatable cushions;
    a pouch formed in one of the end walls of a selected cushions and being connected to each opposite side wall within the cushion but not extending to the opposite end wall thus forming a passageway for the flow of air;
    a bladder insertable into the pouch for exchanging heat with the top surface of the inflatable cushion wherein the bladder contains a conduit loop the ends of which are connected to tubing carrying heat exchange fluid;
    means for circulating heat exchange fluid through the tubing and the bladders;
    means for exchanging heat with the heat exchange fluid.

4. The patient support appliance as set forth in claim 3 further comprising a common outlet fluid manifold connected the circulating means for feeding heat exchange fluid to a plurality of bladders in parallel fashion.

5. The patient support appliance as set forth in claim 4 wherein the bladders are grouped into sets with each bladder of the set being serially connected to the other by means of tubing segments and wherein the sets of bladders are fed heat exchange fluid from the common outlet manifold in parallel fashion.

6. The patient support appliance as set forth in claim 3 wherein each pouch of the selected cushions is stitched all along the length of the pouch to each of the opposite side walls of the cushion.

7. The cushion as set forth in claim 1 wherein the pouch is located closer to the top patient support surface than the bottom of the cushion.

* * * * *